United States Patent
Prandi et al.

(10) Patent No.: US 9,504,504 B2
(45) Date of Patent: *Nov. 29, 2016

(54) SCREW FOR OSTEOSYNTHESIS AND ARTHRODESIS

(71) Applicant: Stryker European Holdings I, LLC, Kalamazoo, MI (US)

(72) Inventors: Bernard Prandi, Rennes (FR); Jean Lariviere, Marq en Baroueul (FR); Mohammed R'Taimate, Peronne en Melantois (FR)

(73) Assignee: Stryker European Holdings I, LLC, Kalamazoo, MI (US)

( * ) Notice: Subject to any disclaimer, the term of this patent is extended or adjusted under 35 U.S.C. 154(b) by 81 days.

This patent is subject to a terminal disclaimer.

(21) Appl. No.: 14/657,308

(22) Filed: Mar. 13, 2015

(65) Prior Publication Data
US 2015/0182271 A1   Jul. 2, 2015

Related U.S. Application Data

(63) Continuation of application No. 13/146,925, filed as application No. PCT/FR2010/000094 on Feb. 9, 2010, now Pat. No. 9,011,505.

(30) Foreign Application Priority Data

Feb. 9, 2009   (FR) ..................................... 09 00557

(51) Int. Cl.
*A61B 17/58* (2006.01)
*A61B 17/86* (2006.01)

(52) U.S. Cl.
CPC ......... *A61B 17/863* (2013.01); *A61B 17/8635* (2013.01); *A61B 17/864* (2013.01)

(58) Field of Classification Search
CPC ............ A61B 17/863; A61B 17/7038; A61B 17/7041; A61B 17/8635; A61B 17/864; F16B 25/103; F16B 25/0084; F16B 25/00; F16B 25/106
USPC .......................... 606/300–321; 411/412–413, 411/387.1–387.8, 386; 433/174, 201.1
See application file for complete search history.

(56) References Cited

U.S. PATENT DOCUMENTS

| 1,677,269 A | 7/1928 | Burghart |
| 2,174,578 A | 10/1939 | Graham |
| 2,242,003 A | 5/1941 | Lorenzo |

(Continued)

FOREIGN PATENT DOCUMENTS

| EP | 0856293 A1 | 8/1998 |
| EP | 1378205 A1 | 1/2004 |

(Continued)

*Primary Examiner* — Anu Ramana
*Assistant Examiner* — Jessica Weiss
(74) *Attorney, Agent, or Firm* — Lerner, David, Littenberg, Krumholz & Mentlik, LLP

(57) ABSTRACT

The invention relates to a self-tapping and self-boring osteosynthesis screw for compressive orthopaedic surgery, characterised in that, in the bone engagement regions, at both the distal portion (A1a) and at the proximal portion (A2a), the sum of the angles defining the outer taper of the shank (f) and the taper of the crest line of the screw thread pitch (P) is higher than 45°, and in that the leading portion (i.e. the most distal one) of each thread includes a plurality of cutting edges (AR) obtained by stock removal.

20 Claims, 3 Drawing Sheets

(56) References Cited

U.S. PATENT DOCUMENTS

| | | | |
|---|---|---|---|
| 2,247,499 A | 7/1941 | Hutchison | |
| 3,512,447 A | 5/1970 | Vaughn | |
| 3,537,288 A | 11/1970 | Ansingh | |
| RE28,111 E | 8/1974 | Laverty | |
| 3,929,054 A | 12/1975 | Gutshall | |
| 4,175,555 A | 11/1979 | Herbert | |
| 4,463,753 A | 8/1984 | Gustilo | |
| 4,537,185 A | 8/1985 | Stednitz | |
| 4,621,963 A | 11/1986 | Reinwall | |
| 4,640,271 A | 2/1987 | Lower | |
| 4,653,244 A | 3/1987 | Farrell | |
| 4,778,319 A | 10/1988 | Schule | |
| 4,940,467 A | 7/1990 | Tronzo | |
| 4,950,270 A | 8/1990 | Bowman et al. | |
| RE33,348 E | 9/1990 | Lower | |
| 5,019,079 A | 5/1991 | Ross | |
| 5,052,719 A | 10/1991 | Boehm | |
| 5,415,507 A | 5/1995 | Janusz et al. | |
| 5,456,685 A | 10/1995 | Huebner | |
| 5,474,408 A | 12/1995 | Dinitz et al. | |
| 5,643,269 A | 7/1997 | Harle | |
| 5,653,710 A | 8/1997 | Harle | |
| 5,746,039 A | 5/1998 | Nystrom | |
| 5,816,012 A | 10/1998 | Willis | |
| 5,827,031 A | 10/1998 | Swallow | |
| 5,857,816 A | 1/1999 | Assmundson | |
| 5,863,167 A | 1/1999 | Kaneko | |
| 5,868,749 A | 2/1999 | Reed | |
| 5,871,486 A | 2/1999 | Huebner et al. | |
| 5,899,906 A | 5/1999 | Schenk | |
| 5,968,047 A | 10/1999 | Reed | |
| 5,997,541 A | 12/1999 | Schenk | |
| 6,004,321 A * | 12/1999 | Graser | 606/53 |
| 6,022,177 A | 2/2000 | Hofer | |
| 6,030,162 A | 2/2000 | Huebner | |
| 6,039,738 A | 3/2000 | Sanders et al. | |
| 6,048,344 A | 4/2000 | Schenk | |
| 6,053,653 A | 4/2000 | Tanaka et al. | |
| 6,074,149 A | 6/2000 | Habermehl et al. | |
| 6,264,677 B1 * | 7/2001 | Simon et al. | 606/232 |
| 6,283,973 B1 | 9/2001 | Hubbard et al. | |
| 6,306,140 B1 * | 10/2001 | Siddiqui | 606/315 |
| 6,319,254 B1 | 11/2001 | Giet et al. | |
| 6,341,917 B1 | 1/2002 | Schubring et al. | |
| 6,402,757 B1 | 6/2002 | Moore, III et al. | |
| 6,436,100 B1 | 8/2002 | Berger | |
| 6,440,136 B1 | 8/2002 | Gambale et al. | |
| 6,635,059 B2 | 10/2003 | Randall et al. | |
| 6,672,791 B2 | 1/2004 | Schubring et al. | |
| 6,736,819 B2 | 5/2004 | Tipirneni | |
| 6,739,815 B2 | 5/2004 | Takasaki | |
| 6,918,727 B2 | 7/2005 | Huang | |
| 6,955,677 B2 | 10/2005 | Dahners | |
| 6,981,974 B2 | 1/2006 | Berger | |
| 7,037,309 B2 | 5/2006 | Weil et al. | |
| 7,044,953 B2 | 5/2006 | Capanni | |
| 7,207,994 B2 | 4/2007 | Vlahos et al. | |
| 7,213,999 B2 | 5/2007 | Haas | |
| 7,316,532 B2 | 1/2008 | Matthys-Mark | |
| 7,367,768 B2 | 5/2008 | McGovern et al. | |
| 7,582,107 B2 | 9/2009 | Trail et al. | |
| 7,591,823 B2 | 9/2009 | Tipirneni | |
| 7,708,738 B2 | 5/2010 | Fourcault et al. | |
| 7,722,654 B2 | 5/2010 | Taylor et al. | |
| 7,731,738 B2 | 6/2010 | Jackson et al. | |
| 7,794,483 B2 | 9/2010 | Capanni | |
| 7,905,909 B2 | 3/2011 | Orbay et al. | |
| 8,070,786 B2 | 12/2011 | Huebner et al. | |
| 8,157,803 B1 | 4/2012 | Zirkle, Jr. et al. | |
| 8,668,725 B2 | 3/2014 | Smisson, III et al. | |
| 2002/0087161 A1 | 7/2002 | Randall et al. | |
| 2002/0169453 A1 | 11/2002 | Berger | |
| 2002/0198527 A1 | 12/2002 | Muckter | |
| 2003/0059270 A1 | 3/2003 | O'Berry | |
| 2003/0078584 A1 | 4/2003 | Tipirneni | |
| 2003/0120277 A1 | 6/2003 | Berger | |
| 2004/0006345 A1 | 1/2004 | Vlahos et al. | |
| 2004/0068261 A1 * | 4/2004 | Fourcault et al. | 606/67 |
| 2004/0172030 A1 | 9/2004 | Tipirrneni | |
| 2004/0172031 A1 | 9/2004 | Rubecamp et al. | |
| 2004/0225292 A1 | 11/2004 | Sasso et al. | |
| 2005/0101961 A1 | 5/2005 | Huebner et al. | |
| 2006/0015105 A1 | 1/2006 | Warren et al. | |
| 2006/0074419 A1 | 4/2006 | Taylor et al. | |
| 2006/0142770 A1 | 6/2006 | Capanni | |
| 2006/0173461 A1 | 8/2006 | Kay et al. | |
| 2006/0217727 A1 * | 9/2006 | Munro et al. | 606/73 |
| 2008/0119855 A1 | 5/2008 | Hoegerle et al. | |
| 2008/0147128 A1 | 6/2008 | Fritzinger | |
| 2008/0188899 A1 | 8/2008 | Bottlang et al. | |
| 2008/0234752 A1 | 9/2008 | Dahners | |
| 2008/0234763 A1 * | 9/2008 | Patterson et al. | 606/315 |
| 2008/0306555 A1 | 12/2008 | Patterson et al. | |
| 2009/0105768 A1 | 4/2009 | Cragg et al. | |
| 2009/0131990 A1 | 5/2009 | Tipirneni et al. | |
| 2009/0198289 A1 | 8/2009 | Manderson | |
| 2009/0254129 A1 | 10/2009 | Tipirneni et al. | |
| 2010/0069970 A1 | 3/2010 | Lewis et al. | |
| 2010/0114315 A1 | 5/2010 | Manderson | |
| 2010/0268285 A1 | 10/2010 | Tipirneni et al. | |

FOREIGN PATENT DOCUMENTS

| | | |
|---|---|---|
| FR | 2840799 A1 | 12/2003 |
| WO | 02056778 A1 | 7/2002 |
| WO | 2004069031 A2 | 8/2004 |

\* cited by examiner

Screw-in direction

Screw-in direction

SCREW FOR OSTEOSYNTHESIS AND ARTHRODESIS

CROSS-REFERENCE TO RELATED APPLICATIONS

The present application is a continuation of U.S. patent application Ser. No. 13/146,925, filed Sep. 6, 2011, which application is a national phase entry under 35 U.S.C. §371 of International Application No. PCT/FR2010/000094, filed Feb. 9, 2010, published as International Publication No. WO 2010/089481 A1, which claims priority from French Patent Application No. 09 00557, filed Feb. 9, 2009, the disclosures of which are incorporated herein by reference.

BACKGROUND OF THE INVENTION

The invention relates to a screw for osteosynthesis and arthrodesis for orthopedic surgery.

It finds a particularly important, although not exclusive, application in the field of anchors for orthopedic surgery of the hand and of the foot, more particularly at the phalanxes of the fingers and of the toes, but also of the metacarpals and metatarsals and notably for corrective surgery for the hand and for the foot.

Note than an osteosynthesis anchor must be used to keep in place two (or more) portions of one and the same bone fractured or cut by a surgical operation (osteotomy) for the time necessary for this bone to consolidate (typically three months).

An arthrodesis for its part is the immobilization of an articulation by surgical means in order to weld two bones into a single bone, by means of an osteosynthesis device.

In general the object of any osteosynthesis, and particularly in the case of an arthrodesis, is to seek a very good stability of the anchor in order to obtain the consolidation in the best conditions, that is to say in the position chosen by the surgeon, while minimizing the problems of postoperative pain and edemas, and while shortening the consolidation time as much as possible.

In order to obtain this result, the shape of the anchor is critical.

Another object sought is to provide and maintain a slight compression between the portions of bone to be fused, which makes the consolidation easier. Here again the shape of the anchor is important.

Various technical solutions have already been proposed for achieving such an osteosynthesis, notably at the extremities (foot, hand, wrist, ankle, etc.).

In addition to the conventional or shape-memory staples, it is for example routine to use screws, notably double-pitch screws allowing the placing in compression. In these screws, the pitch of each end is different (distal pitch and proximal or head pitch), for example 0.25 mm per rotation, which makes it possible to obtain a compression of 1 mm in 4 rotations. These known screws may be tubular (mounting on a pin) or not. They are usually self-tapping, that is to say that they do not usually require drilling.

Document FR 2 840 799 describes a self-tapping screw in the distal portion, for which it is nevertheless often necessary to carry out a real pre-drilling notably in the proximal portion which takes away the value of the self-drilling. Moreover, the cutting ridges of the threads are defined at the bore, which weakens the screw, that is to say that in practice the teeth thus defined break very easily.

A second frequent problem with these screws is that their length must be perfectly suited to the bony site so as not to create discomfort, and therefore that they must be screwed immediately in contact with the bone without pushing the latter away at the distal end, while ensuring a good anchorage of the end, which means a cylindrical end making good penetration impossible.

Therefore a screw is known (U.S. Pat. No. 6,306,140) comprising three portions, namely a cylindrical tapped distal portion, a smooth central portion and a self-tapping tapped proximal or head portion of larger diameter.

Such a screw has a particular angular condition only at the head, the distal portion therefore being conventional for its part, that is to say with the ridges of the screwthread being inscribed in a cylinder.

Document EP 0 856 293 A1 describes for its part a screw which on this occasion is self-tapping and self-drilling but which, in order to do this, has bevels at the ends which on the other hand detracts from the grip of the screw or makes it necessary to sink it more deeply in order that the bone is at the level at which the screw is totally cylindrical. Moreover, the proposed cutting ridges are too deep, fragile and therefore breakable at the barrel.

The invention provides a remedy for all these drawbacks in a simple, reliable, effective and rational manner.

To do this, the object of the present invention is to propose a screw that satisfies better than those formerly known the requirements of the practice notably in that it proposes a self-drilling and self-tapping, compressive screw allowing a good penetration and simultaneously ensuring a very good bone anchoring and does so without passing through the bone.

Such a screw is specially adapted to the surgical techniques that bear on the two sides of a fairly thin cortical bone as in the case of a metatarsal osteotomy of the "scarf" type.

In the rest of the text, reference will be made to the following definitions:

distal end of the screw: corresponds to the portion that first comes into contact with the bone;
proximal (or head) end: corresponds to the portion that is screwed in last and that comprises the connection to a screwing means (screwdriver for example);
barrel of the screw: corresponds to the core or generally cylindrical portion on which the screwthread is positioned.

For this purpose, the invention therefore notably proposes an osteosynthesis and arthrodesis screw for orthopedic surgery notably of the hand and of the foot, the screw being tubular or not, having along its main axis (AP) three successive portions, namely a distal portion comprising threads (A1), a smooth central portion or central barrel (f) and a proximal portion or head comprising threads (A2), the distal portion having an external diameter that is slightly smaller than that of the proximal portion and having a screw pitch that is slightly greater than that of the proximal portion, making it possible to place in compression the two bony portions to be fused together, the bone-attack zone in the proximal portion (A2a) being conical self-tapping, characterized in that the end of the distal portion is conical, in that the sum of the angles a1+b1 at the distal end and a2+b2 at the proximal end, defined between, on the one hand, the main axis (AP) of the screw and the external conicity of the barrel ((f1) at the distal end and (f2) at the proximal end), namely (a1) at the distal end, (a2) at the proximal end and, on the other hand, between the main axis (AP) of the screw and the crest line of the threads (P) of the screwthread, namely (b1) at the distal end and (b2) at the proximal end, is greater than 45°, and in that the attack portion, that is to say the most distal of each thread, has a plurality of cutting ridges (AR) obtained by removal of material.

"Diameter slightly less than" means a difference of between one fifth and one twentieth of the diameter of the proximal portion and advantageously and for example a diameter of the distal portion equal to the order of nine tenths of the diameter of the proximal portion.

"Screw pitch slightly greater than" means a screw pitch of the distal portion greater than a value of between 5% and 20%, and advantageously of the order of 10%, of the screw pitch of the proximal portion.

The two threaded zones, whether they be distal or proximal, for their part make it possible to achieve the bony anchorage, each of the two threads being self-drilling and self-tapping.

The invention is based on the idea of achieving in combination two anchoring zones biting into the bone when screwed in, one for the proximal portion and the other for the distal portion, with particular external profiles, namely slightly conical (thinner on the distal side) out of which the also conical threads are cut, both of them, at the distal end and at the proximal end, comprising several cutting ridges each made by a longitudinal cut in the screwthread.

More precisely, in the embodiment that is more particularly described here, the distal portion, the body of which is of slight conicity (the angle a1 for example being between 4 and 15°), is furnished with a thread of great conicity (the angle b1 for example being between 50 and 80°) so that the profile of the crest of the threads of the end of the distal portion becomes cylindrical after the first or the second thread (see FIG. 2a).

Such an arrangement combined with ridges that are particularly cutting by reason of their formation by removal of material, allows the end to play a role of a punch which immediately catches hold and which makes it possible to place the screw without pre-drilling in a soft bone or with a slight punching in the bone in a harder bone, while having the same anchoring capacity as a screw with a purely cylindrical crest profile.

It is evident moreover that the fact that the ridges are obtained by removal of material and the fact that the profiles are specific and as described hereinabove surprisingly allow not only a good immediate penetration in the two portions of the bone, but also a good compression of the two portions of bone against one another and finally a good hold in the bone itself, and this is despite the conicity of the distal portion of the screw, and without passing through the bone.

The assembly can be anchored via the conventional manner of screws, after stabilization of the osteotomy by any appropriate instrument (tongs or forceps) and with the aid of an appropriate screwdriver, mounted on a pin (tubular screw) or not (solid), or a screw fitting making it possible to be connected to a motor.

Moreover, to take account of the anatomical characteristics, the anchoring zones are advantageously connected to the middle zone that is used for strength (notably shear strength) at the osteosynthesis focal point by more or less long connection zones.

Finally, the material constituting the anchor that is the subject of the invention allows drilling in the bone and therefore has the necessary hardness. Any anchorable material that is sufficiently hard such as stainless steel, titanium, a CrCo (chrome-cobalt) alloy, etc. is advantageously chosen in this instance.

In a particular embodiment of the invention, the anchor is therefore notably made of a titanium alloy such as the alloy known as TA6V (titanium, aluminum, vanadium alloy).

In advantageous embodiments, use is also made of one and/or the other of the following arrangements:

the cutting ridges (AR) are offset negatively relative to a radial axis of the screw, that is to say rearward relative to the direction of rotation of the screw when screwing in;

the cutting ridges (AR) are offset rearward in order to present a bone attack angle when screwing in (C) (at the distal end and at the proximal end) of between 5° and 12°;

the cutting ridges (AR) are preferably three in number;

the depth of the cutting ridges (AR) is less than or equal to the depth of the screwthread;

the depth of the cutting ridges (AR) is equal to the depth of the screwthread;

the sum of the angles (a1+b1) at the distal end and (a2+b2) at the proximal end, respectively is between 50° and 70°;

the angle (a1) at the distal end is between 4° and 10° and the angle (a2) at the proximal end is between 10° and 20°;

the cutting ridges (AR) have a relief of approximately 10° rearward in the direction of screwing in;

the screw has a flat or conical head.

BRIEF DESCRIPTION OF THE DRAWINGS

The invention will be better understood on reading the following description of an embodiment given as a nonlimiting example.

The description refers to the attached drawings in which.

DETAILED DESCRIPTION

Figure 1:
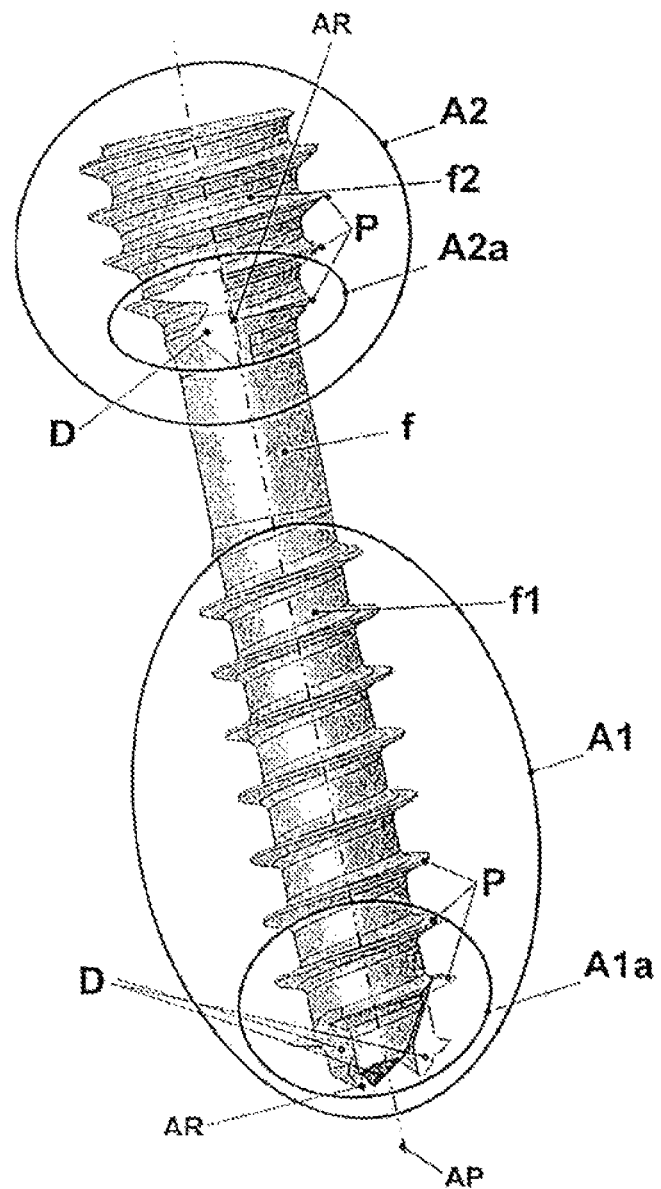
FIG. 1 is a side view of a screw according to a first embodiment of the invention.

FIG. 1 shows a general view of the screw according to the embodiment of the invention most particularly described here, which shows two anchoring zones, namely a distal portion A1 and a proximal portion A2. The core formed with the screwthread, also called the barrel f, is generally cylindrical. For consistency, f1 is the portion of the barrel of the zone A1 at the distal end A1, that is to say the body of the screw except for the threads, and f2 is the portion of the barrel of the zone A2 at the proximal end A2. Each zone A1 and A2 has threads P and forms an attack zone (the first to come into contact with the bone and to bite into it when screwing in) A1a at the distal end, and A2a at the proximal end followed by a screwing zone.

The distal and proximal attack zones A1a and A2a each comprise several teeth D, for example three teeth each defining a cutting ridge AR. These teeth D are formed by a notch or cut parallel to a main axis AP of the screw in order to create a cutting ridge AR at the intersection of this milling with the outer edge of the thread of the screw P.

Figure 2A:
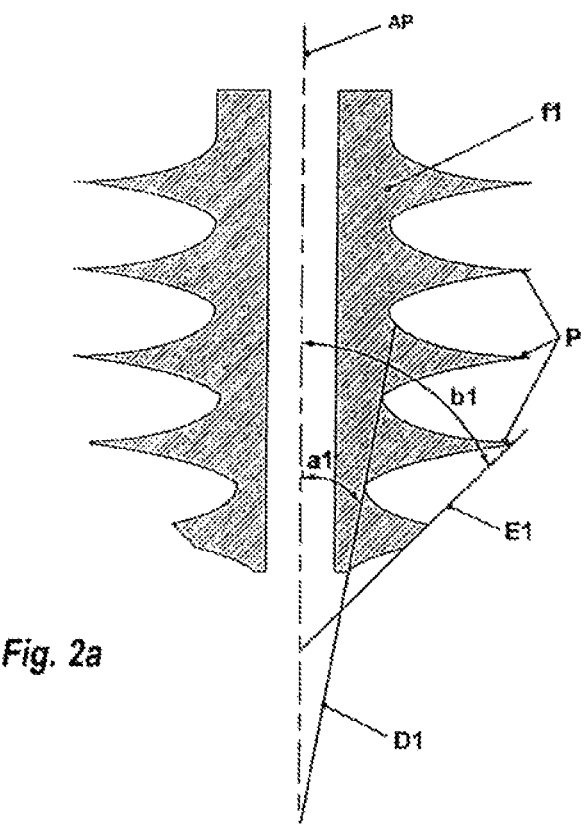
FIGS. 2a and 2b are views in longitudinal section along the main axis of the screw, respectively of the distal portion and of the proximal portion.

FIG. 2a shows more precisely a longitudinal section of the screw in the distal portion.

In this section, a1 is defined as the angle between the main axis AP and a straight line D1 connecting the roots of the threads P, or corresponding to the external surface of the barrel f1 excluding the threads. The angle b1 is also defined as the angle between the main axis AP and the straight line E1 connecting the crests of the threads P.

Figure 2B:
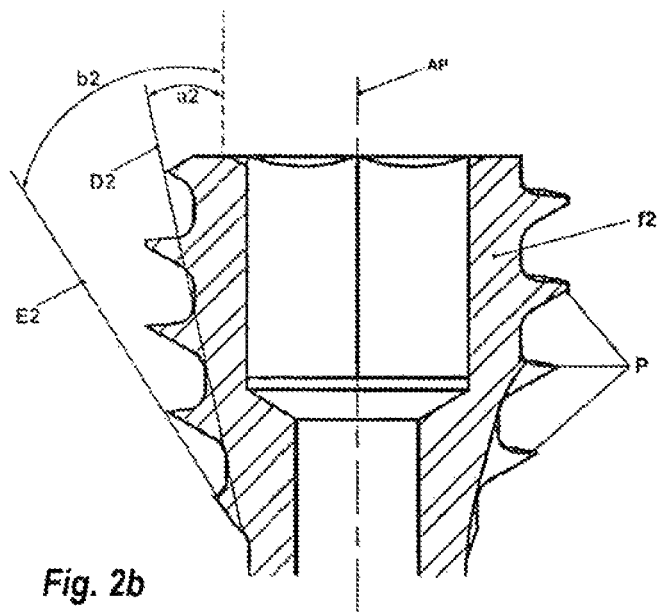

In the same manner, FIG. 2b shows a longitudinal section of the screw in the proximal portion. In this section, a2 is defined as the angle between the main axis AP and the straight line D2 connecting the roots of the threads P, or corresponding to the external surface of the barrel f2 excluding the threads.

Also the angle b2 is defined as the angle between the main axis AP and the straight line E2 connecting the crests of the threads P.

Figure 3A:
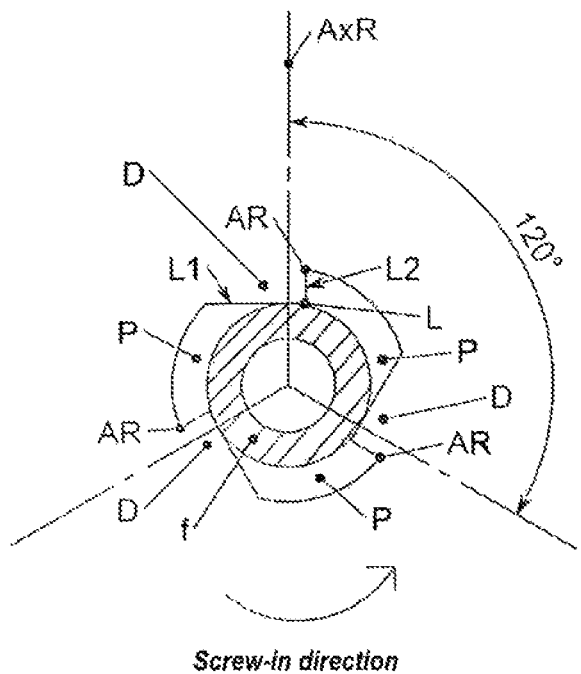
FIGS. 3a and 3b are cross sections at the cutting ridges in a reference position (FIG. 3a) and after a slight screwing in (approximately ⅓₀th of a turn) (FIG. 3b).

FIG. 3a for its part shows a cross section of the screw in the zone A1a, that is to say at the teeth D. The section is identical in the zone A2a and is therefore not shown. The cross-hatched zone f corresponds to the tubular barrel of the screw. The teeth D are shown to be three in number, and produced by removal of material corresponding to a ½ rectangle (L1-L2). The cutting ridges AR correspond to the intersection of the side L2 with the outside of the thread P. AxR is a radial axis of the screw.

Figure 3B:
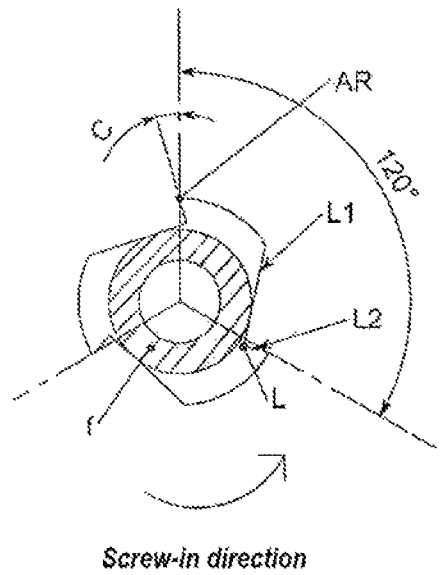

FIG. 3b shows the same section after a slight rotation through an angle C. This angle C corresponds to the angle between the radial axis AxR passing through the cutting ridge AR and the side L2.

In order to obtain proper penetration, the distal end of the barrel, namely f1 at the distal end and f2 at the proximal end (corresponding to the thread bottoms), is slightly conical, both at the distal end A1a and at the proximal end A2a, with an angle a1 at the distal end and a2 at the proximal end.

This conicity of the barrel f is associated with a conicity of the crest of the thread angle b1 at the distal end and b2 at the proximal end that are large enough to allow an immediate engagement of the screw as soon as perforation begins.

Specifically the thread of the screw is cut at the very bottom of the end A1a at the distal end A2a at the proximal end, respectively on this conical trajectory, that is to say that the thread depth increases very rapidly which makes it possible to have a significant thread height as close as possible to the end.

According to the embodiment of the invention that is more particularly described here, on the one hand the sum of the angles a1+b1 at the distal end, a2+b2 at the proximal end, defined between on the one hand the main axis of the screw AP and the external conicity of the barrel f1 at the distal end and f2 at the proximal end, a1 at the distal end, a2 at the proximal end, and, on the other hand, between the main axis of the screw AP and the crest line of the threads P of the screwthread, namely b1 at the distal end, b2 at the proximal end, is greater than 45° and on the other hand the attack portion (the most distal portion) of each thread has a plurality of cutting ridges AR obtained by removal of material.

Moreover, and as has been seen, in advantageous embodiments, the cutting ridges AR are three in number, the sum of the angles (a1+b1 at the distal end and a2+b2 at the proximal end, respectively) is between 50° and 70°, and/or the angle a1 at the distal end is between 4° and 10° and the angle a2 at the proximal end is between 10° and 20°.

In practice, and as a nonlimiting example, for a screw of 2 mm in diameter, the distal diameter of the distal end is 1.8 mm to allow good penetration. The angle a1 is 6°, the angle a2 is 15°, while b1 is fixed at 50° and b2 at 40° to allow immediate anchoring. That is to say a1+b1=56° and a2+b2=55°.

In cross section, the cutting ridges are obtained by the machining of a closed L by the external diameter of the thread P of the screw.

This L is formed by a long side L1 and a short side L2 (FIG. 3).

Finally, so as not to weaken the screw, the position of the point of intersection of the straight-line sides L1 and L2 (point L), that is to say the depth of the cut, in no circumstances bites into the main barrel.

In the advantageous embodiment more particularly described, the depth of the cutting ridges AR is less than or equal to the depth of the screwthread.

Finally, in FIG. 3a, the position of the plane defined in cross section by the straight line L2 where it intersects the thread represents the cutting ridge AR is offset rearward (or negatively) (in the screwing-in direction), to a radial axis of the screw AxR so that, when turning as can be seen in FIG. 3b, these ridges AR attack the bone with an angle C, defined in cross section between the radial axis passing through AR and the straight line L2.

It will be similarly noted with reference to FIG. 3a that the cutting ridges AR are offset negatively relative to an axis radial to the screw, that is to say rearward relative to the direction of rotation of the screw when screwing in, for example the cutting ridges AR are offset rearward in order to have a bone attack angle C when screwing in (at the distal and proximal ends) of between 5° and 12°.

In practice, as an example for a screw with a nominal diameter of 2.5 mm, a slight offset of 0.15 mm makes it possible to obtain an angle C of 7°.

In order to improve the clearance of bone chips, a relief of 10° rearward in the direction of screwing in can be made on each tooth D.

Also the external end of the head may be completely conical, for penetrating into the bone, or have a flat head in order to press on the external surface of the bone.

Now, with reference to FIG. 1, installation of a screw according to the invention will be described.

The surgeon will first of all bring together the two pieces of bone placing them next to one another in their fusion position.

Then, without initial preparation or pre-tapping, he will screw the screw through the bone portion known as the upper bone portion.

Since the distal portion is conical, penetration takes place until the proximal portion remains in contact with the bone.

The different pitches of the screws then have an effect of bringing together and of compressing the bone portions, which effect is increased at the end of screwing in by the conical aspect of the ends of the two distal and proximal portions in an increased manner.

Astonishingly, the combination of the two conical-effect screw formations, as described above, increases the stability of the assembly and allows an exceptional consolidation.

It goes without saying and it results from the foregoing that the present invention is not limited to the embodiments more particularly described. On the contrary, it covers all the variants thereof.

The invention claimed is:

1. A screw for insertion into bone comprising:
   a shaft having a proximal portion defining a screw head, and a distal portion and an unthreaded portion between the proximal and the distal portions, the shaft defining a central axis through the proximal and the distal portions;
   proximal threads extending along an outer surface of the proximal portion of the shaft; and
   distal threads extending along an outer surface of the distal portion of the shaft, the distal threads having crests at their outer extremities, the outer surface of the distal portion of the shaft defining roots of the distal threads,
wherein bottom-most points of two adjacent roots of the distal threads define a root line,
wherein tips of two adjacent crests of the distal threads define a crest line,
wherein the root line and the crest line intersect the central axis,
wherein the central axis and the root line define an angle a1, and the central axis and the crest line define an angle b1, and
wherein the sum of the angles a1+b1 is greater than 45°.

2. The screw as claimed in claim 1,
wherein the outer surface of the proximal portion of the shaft defines roots of the proximal threads, bottom-most points of two adjacent roots of the proximal threads defining a second root line,
wherein the proximal threads have crests at their outer extremities, tips of two adjacent crests of the proximal threads defining a second crest line,
wherein the central axis and the second root line define an angle a2,
wherein the central axis and the second crest line define an angle b2, and
wherein the sum of the angles a1+b1 is between 50° and 70°, and the sum of the angles a2+b2 is between 50° and 70°.

3. The screw as claimed in claim 2, wherein the angle a1 is between 4° and 10°, and the angle a2 is between 10° and 20°.

4. The screw as claimed in claim 1, wherein the proximal portion of the shaft is conical and the proximal threads are self-tapping such that the proximal portion and the proximal threads provide a bone-attack zone.

5. The screw as claimed in claim 1, wherein a distal attack portion of the distal threads comprises a plurality of cutting ridges obtained by removal of material on the respective threads.

6. The screw as claimed in claim 5, wherein each cutting ridge is offset from a respective radial axis of the shaft, the radial axis being perpendicular to the central axis and intersecting an outermost location of the respective cutting ridge, such offset being in a direction from the radial axis opposite the direction of rotation of the screw during screw insertion.

7. The screw as claimed in claim 6, wherein each cutting ridge is offset 10° from the respective radial axis of the shaft.

8. The screw as claimed in claim 6, wherein each cutting ridge is offset from the radial axis in order to present, during insertion of the screw, a bone attack angle relative to the radial axis of between 5° and 12°.

9. The screw as claimed in claim 5, wherein a depth of the cutting ridges is less than or equal to a depth of the respective thread on which each cutting ridge is formed.

10. The screw as claimed in claim 1, wherein the screw head is flat on an external end thereof for pressing onto an external surface of bone.

11. The screw as claimed in claim 1, wherein each of the proximal and distal portions of the shaft are conical.

12. The screw as claimed in claim 1, wherein the distal threads have a first screw pitch and the proximal threads have a second screw pitch that is different than the first screw pitch.

13. The screw as claimed in claim 12, wherein the first screw pitch is greater than the second screw pitch.

14. The screw as claimed in 1,
wherein the outer surface of the proximal portion of the shaft defines roots of the proximal threads, the roots of the proximal threads defining a second root line,
wherein the proximal threads have crests at their outer extremities, the crests of the proximal threads defining a second crest line,
wherein the central axis and the second root line define an angle a2,
wherein the central axis and the second crest line define an angle b2,
wherein the second root line and the second crest line intersect the central axis, and
wherein the sum of the angles a1+b1 is greater than the sum of the angles a2+b2.

15. A screw for insertion into bone comprising:
a shaft having a proximal portion defining a screw head', a distal portion, and an unthreaded portion between the proximal and the distal portions, the shaft defining a central axis through the proximal and distal portions;
proximal threads extending along an outer surface of the proximal portion of the shaft; and
distal threads extending along an outer surface of the distal portion of the shaft, the distal threads having crests at their outer extremities,
wherein tips of two adjacent crests of the distal threads define a line intersecting the central axis,
wherein the central axis and the line define an angle between 50° and 80°.

16. The screw as claimed in claim 15, wherein a distal attack portion of each of the proximal and distal threads comprises a plurality of cutting ridges obtained by removal of material on the respective threads, wherein each cutting ridge is offset from a respective radial axis of the shaft, the radial axis being perpendicular to the central axis and intersecting an outermost location of the respective cutting ridge, such offset being in a direction from the radial axis opposite the direction of rotation of the screw during screw insertion.

17. The screw as claimed in claim 15, wherein the proximal portion of the shaft is conical and the proximal threads are self-tapping such that the proximal portion and the proximal threads provide a bone-attack zone.

18. A screw for insertion into bone comprising:
a shaft having a proximal portion defining a screw head and a distal portion, the shaft defining a central axis through the proximal and distal portions;
distal threads extending along a distal outer surface of the distal portion of the shaft, the distal threads having crests at their outer extremities, the outer surface of the distal portion of the shaft defining roots of the distal threads, the distal threads defining crests at their outer extremities opposite the roots;
proximal threads extending along a proximal outer surface of the proximal portion of the shaft, the proximal threads having crests at their outer extremities, the outer surface of the proximal portion of the shaft defining roots of the proximal threads;
wherein at least two of the roots of the distal threads define a distal root line,
wherein at least two of the crests of the distal threads define a distal crest line,
wherein the central axis and the distal root line define an angle a1, and the central axis and the distal crest line define an angle b1,
wherein at least two of the roots of the proximal threads define a proximal root line, wherein at least two of the crests of the proximal threads define a proximal crest line, wherein the distal root line, the distal crest line, the proximal root line, and the proximal crest line intersect the central axis, wherein the central axis and the proximal root line define an angle a2, and the central axis and the proximal crest line define an angle b2, and wherein the sum of the angles a1+b1 is greater than 45°, and the sum of the angles a2+b2 is between 50° and 70°.

19. The screw as claimed in claim 18, wherein the shaft includes an unthreaded portion between the distal and proximal threads.

20. The screw as claimed in claim 18, wherein the distal threads have a first screw pitch and the proximal threads have a second screw pitch that is different than the first screw pitch.

\* \* \* \* \*